(12) United States Patent
Soma et al.

(10) Patent No.: US 7,485,698 B2
(45) Date of Patent: Feb. 3, 2009

(54) PHARMACEUTICAL COMPOSITION FOR PREVENTING OR TREATING MALIGNANT GLIOMA

(75) Inventors: Gen-Ichiro Soma, 10-21, Higashitamagawa 1-chome, Setagaya-ku, Tokyo (JP); Hiroyuki Inagawa, Yamaguchi (JP); Chie Kohchi, Hiroshima (JP); Takashi Nishizawa, Tokushima (JP)

(73) Assignee: Gen-Ichiro Soma (JP)

( * ) Notice: Subject to any disclaimer, the term of this patent is extended or adjusted under 35 U.S.C. 154(b) by 0 days.

(21) Appl. No.: 11/413,751

(22) Filed: Apr. 28, 2006

(65) Prior Publication Data
US 2007/0059279 A1   Mar. 15, 2007

Related U.S. Application Data

(63) Continuation of application No. PCT/JP2004/016096, filed on Oct. 29, 2004.

(30) Foreign Application Priority Data
Oct. 31, 2003   (JP) .............................. 2003-372659

(51) Int. Cl.
*A61K 38/00* (2006.01)
*A01N 37/18* (2006.01)

(52) U.S. Cl. .......................................... 530/350; 514/2
(58) Field of Classification Search ........................ None
See application file for complete search history.

(56) References Cited

U.S. PATENT DOCUMENTS
2004/0121971 A1   6/2004   Chen et al.

FOREIGN PATENT DOCUMENTS
CN   1509763   7/2004

OTHER PUBLICATIONS

Gura, Science, 1997, 278:1041-1042.*
Kaiser, Science, 2006, 313, 1370.*
Omuro et al, Mol Cancer Ther, 2007, 6:1909-1919.*
Bowie et al, Science, 1990, 257:1306-1310.*
Burgess et al, J of Cell Bio. 111:2129-2138, 1990.*
Lazar et al, Molecular and Cellular Biology, 1988, 8:1247-1252.*
Ben-Efraim, Tumor Biology 1999; 20: 1-24.*
Marincola et al., Trends in Immunology 2003; 24: 334-341.*
Frazer, I., Expert. Opin. Pharmacother. 2004; 5: 2427-2434.*
Yoshida et al, J Neurosurg, 1992, 77:78-83.*

* cited by examiner

*Primary Examiner*—Misook Yu
*Assistant Examiner*—Mark Halvorson
(74) *Attorney, Agent, or Firm*—Lahive & Cockfield LLP; Giulio A. DeConti, Jr.; Megan E. Williams

(57) ABSTRACT

An object of the present invention is to provide a novel malignant glioma antitumor agent and malignant glioma antitumor agent for animals, and in order to achieve this object, in the present invention a polypeptide indicated by the following (a) or (b), or a mixture thereof, is contained in a malignant glioma antitumor agent:

(a) a polypeptide comprising the amino acid sequence represented by SEQ. ID NO. 1 or SEQ. ID NO. 2; or
(b) a polypeptide comprising the amino acid sequence represented by SEQ. ID NO. 1 or SEQ. ID NO. 2 with 1 or more amino acids deleted, substituted or added, and which has malignant glioma antitumor action.

6 Claims, No Drawings

PHARMACEUTICAL COMPOSITION FOR PREVENTING OR TREATING MALIGNANT GLIOMA

CROSS-REFERENCE TO RELATED APPLICATIONS

This application is a continuation of PCT/JP2004/016096, filed on Oct. 29, 2004, which in turn claims priority from Japanese application no. JP 2003-372659 filed on Oct. 31, 2003, the contents of which are incorporated herein by reference.

STATEMENT REGARDING FEDERALLY SPONSORED RESEARCH OR DEVELOPMENT

THE NAMES OF THE PARTIES TO A JOINT RESEARCH AGREEMENT

INCORPORATION-BY-REFERENCE OF MATERIAL SUBMITTED ON A COMPACT DISC.

BACKGROUND OF THE INVENTION

Tumors consist of a collection of cells that demonstrate autonomous hyperplasia. Although they are categorized as malignant tumors (or so-called cancers), which have the potential of causing death of the tumor-laden animal, and benign tumors, which do not have such potential, there are numerous exceptions and it is difficult to strictly distinguish between the two (Iwanami Biology Encyclopedia, 3rd Edition, page 4).

The three pillars of current cancer therapy consist of surgical therapy, chemotherapy and radiotherapy, and more realistically, multidisciplinary therapy that combines the above treatments with laser therapy and so on is widely performed. In consideration of the pain associated with therapy and metastasis, it is only natural to place considerable expectations on chemotherapy, and although numerous antitumor agents have been developed and are used to respond to these expectations, none are effective against all tumors. In addition, many antitumor agents are unable to demonstrate adequate effects when used alone or cannot be used for an extended period of time due to severe adverse side effects, and multiple agents are typically used in combination. Thus, there are considerable expectations being placed on the development of a new antitumor agent, and particularly that which has potent anticancer effects and which can be used for an extended period of time by a simple method.

Anticancer agents that are effective against brain tumors in particular have yet to be discovered. According to the Guidelines for the Treatment of Brain Tumors (Kanehara & Co., Ltd., published on Jul. 31, 2002), the total number of cases of brain tumors from 1969 to 1993 exceeded 81,000, and the approximate number of affected persons is estimated to be about 8 to 10 per 100,000 persons.

Primary brain tumors are classified into more than 10 types according to their origin of onset and pathological tissue type, examples of which include glioma and meningioma. Gliomas are particularly serious in terms of both incidence and malignancy, and are classified into seven or more types such as glioblastoma and anaplastic astrocytoma according to their detailed pathological tissue type. Disease stage (tumor size, presence of distal metastasis) and histological malignancy are used when determining the degree of malignancy of primary brain tumors. Histological malignancy is classified into four levels consisting of G1 to G4 according to the Guidelines for the Treatment of Brain Tumors (op cit.), and these correspond to WHO1 to WHO4, respectively. The larger the number, the higher the degree of malignancy. For example, the malignancy of glioblastoma is G4 (WHO4), while the malignancy of anaplastic astrocytoma is G3 (WHO3), and both G3 and G4 are classified as malignant. Thus, those primary brain tumors that should first be targeted by anti-brain tumor agents are gliomas, and particularly glioblastoma or anaplastic astrocytoma associated with a high degree of malignancy.

Gliomas are tumors that occur in the brain parenchyma and demonstrate invasive growth, and it is difficult to achieve a complete cure with surgery alone. Glioblastomas in particular are the most resistant to treatment, and have an extremely poor five-year survival rate of about 8%. Although definitive efficacy of chemotherapy has only been confirmed for alkylating agents and temozolomide, their efficacy is limited to concomitant use with radiotherapy. On the other hand, post-surgical radiotherapy has been recognized to demonstrate life-prolonging effects.

TNF-$\alpha$ has been previously reported to have a certain degree of antitumor effects against brain tumors when used in special forms of therapy. For example, antitumor effects have been reported to be obtained against glioblastoma during local injection of TNF-$\alpha$ (Hayashi, S. et al.: Clinical significance of the expression of nuclear factor-kappa B, tumor necrosis factor receptor type I (TNFR I, and c-mycin in human malignant astrocytomas", Neurol. Med. Chir., 2001, Vol. 41, pp. 187-195), and a certain degree of antitumor effects have been reported to be obtained following intra-arterial injection of TNF-$\alpha$ (Harada, K. et al.: "Antitumor effect of intra-arterial tumor necrosis factor-alpha in rats with transplanted intracerebral glioma and its evaluation by MRI", Japan J. Neurosurgery, 1995, Vol. 23, pp. 1069-1074).

However, in the case of administration of TNF-$\alpha$, even if antitumor effects are obtained, there is the problem of these effects not leading to life-prolonging effects, and there are in fact no reports describing the obtaining of life-prolonging effects in brain tumor patients administered TNF-$\alpha$. In addition, life-prolonging effects have also not been observed in glioblastoma rats administered TNF-$\alpha$.

On the other hand, although polypeptides represented by X—X'—(amino acid sequence of the fourth exon portion of TNF) (wherein, X represents a single hydrogen atom or a peptide for which the type and number can be determined arbitrarily, X' represents a peptide having 1 to 39 amino acid residues, and the ratio of the number of net basic amino acid residues to the number of amino acid residues that compose X and X' exceeds 14.5%) (Japanese Patent No. 2544114), and polypeptides composed of the amino acid sequence described in SEQ. ID NO. 1 or 2 (Japanese Patent Publication No. H8-17716) are known to have antitumor action, these polypeptides are not known to have malignant glioma antitumor action.

BRIEF DESCRIPTION OF THE SEVERAL VIEWS OF THE DRAWING(S)

BRIEF SUMMARY OF THE INVENTION

An object of the present invention is to provide a novel pharmaceutical composition for preventing or treating malignant glioma and a novel a pharmaceutical composition for preventing or treating malignant glioma for animals.

In order to solve the above-mentioned problems, the present invention provides the following pharmaceutical composition for preventing or treating malignant glioma.

(1) A pharmaceutical composition for preventing or treating malignant glioma comprising a polypeptide shown in (a) or (b) below, or a mixture thereof:
(a) a polypeptide comprising the amino acid sequence represented by SEQ. ID NO. 1 or SEQ. ID NO. 2; or
(b) a polypeptide comprising the amino acid sequence represented by SEQ. ID NO. 1 or SEQ. ID NO. 2 with 1 or more amino acids deleted, substituted or added, and which has malignant glioma antitumor action.

(2) The pharmaceutical composition according to (1) above, wherein the polypeptide shown in (b) above is a polypeptide comprising the amino acid sequence represented by SEQ. ID NO. 1 or SEQ. ID NO. 2 with 1 or more amino acids deleted, substituted or added in the region ranging from 1st to 18th amino acid of the amino acid sequence represented by SEQ. ID NO. 1 or SEQ. ID NO. 2.

(3) The pharmaceutical composition according to (1) or (2) above, which is a pharmaceutical composition for animals.

(4) A method for preventing or treating malignant glioma comprising: administering to humans or animals a polypeptide shown in (a) or (b) below, or a mixture thereof:
(a) a polypeptide comprising the amino acid sequence represented by SEQ. ID NO. 1 or SEQ. ID NO. 2; or
(b) a polypeptide comprising the amino acid sequence represented by SEQ. ID NO. 1 or SEQ. ID NO. 2 with 1 or more amino acids deleted, substituted or added, and which has malignant glioma antitumor action.

(5) The method according to (4) above, wherein the polypeptide shown in (b) above is a polypeptide comprising the amino acid sequence represented by SEQ. ID NO. 1 or SEQ. ID NO. 2 with 1 or more amino acids deleted, substituted or added in the region ranging from 1st to 18th amino acid of the amino acid sequence represented by SEQ. ID NO. 1 or SEQ. ID NO. 2.

(6) Use of a polypeptide shown in (a) or (b) below, or a mixture thereof, to produce a pharmaceutical composition for preventing or treating malignant glioma:
(a) a polypeptide comprising the amino acid sequence represented by SEQ. ID NO. 1 or SEQ. ID NO. 2; or
(b) a polypeptide comprising the amino acid sequence represented by SEQ. ID NO. 1 or SEQ. ID NO. 2 with 1 or more amino acids deleted, substituted or added, and which has malignant glioma antitumor action.

(7) The use according to (6) above, wherein the polypeptide shown in (b) above is a polypeptide comprising the amino acid sequence represented by SEQ. ID NO. 1 or SEQ. ID NO. 2 with 1 or more amino acids deleted, substituted or added in the region ranging from 1st to 18th amino acid of the amino acid sequence represented by SEQ. ID NO. 1 or SEQ. ID NO. 2.

DETAILED DESCRIPTION OF THE INVENTION

A pharmaceutical composition of the present invention comprises a polypeptide indicated by the following (a) or (b), or a mixture thereof:
(a) a polypeptide comprising the amino acid sequence represented by SEQ. ID NO. 1 or SEQ. ID NO. 2 (to be referred to as polypeptide (a)); or
(b) a polypeptide comprising the amino acid sequence represented by SEQ. ID NO. 1 or SEQ. ID NO. 2 with 1 or more amino acids deleted, substituted or added, and which has malignant glioma antitumor action (to be referred to as polypeptide (b)).

In the amino acid sequence represented by SEQ. ID NO. 1 or SEQ. ID NO. 2, the portion from the 19th amino acid (Ala) to the amino acid on the C terminal (Leu) corresponds to the amino acid sequence of the 4th exon of human TNF-α. Namely, in the case of adding guanine to the 5' end of DNA encoding the 4th exon of human TNF-α (see SEQ ID NO: 3), the sequence is identical to the amino acid sequence of the resulting encoded polypeptide.

There are no particular limitations on the number of amino acids deleted, substituted or added in the amino acid sequence represented by SEQ ID NO: 1 or SEQ ID NO: 2 provided that malignant glioma antitumor action is retained, that number is one or more, and the specific range relating to deletion or substitution is normally 1 to 14 and preferably 1 to 2, while the specific range relating to addition is normally 1 to 45, preferably 1 to 39, and more preferably 1 to 6.

Although there are no limitations on the location where one or a plurality of amino acids are deleted, substituted or added in the amino acid sequence represented by SEQ ID NO: 1 or SEQ ID NO: 2 provided malignant glioma antitumor action is retained, preferably one or a plurality of amino acids are deleted, substituted or added in the portion from the 1st amino acid residue (Met) to the 18th amino acid residue (Val), while one or a plurality of amino acids are not deleted, substituted or added in the portion from the 19th amino acid (Ala) to the amino acid of the C terminal (Leu). This is because, in a polypeptide composed of the amino acid sequence represented by SEQ ID NO: 1 or SEQ ID NO: 2, the N terminal is thought to not be involved in steric structure, while the C terminal is thought to be involved in steric structure.

There are no particular limitations on the number of amino acids deleted, substituted or added in the portion from the 1st amino acid residue (Met) to the 18th amino acid residue (Val) provided malignant glioma antitumor action is retained, that number is one or more, the specific range relating to deletion or substitution is normally 1 to 14 and preferably 1 to 2, while the specific range relating to addition is normally 1 to 45, preferably 1 to 39, and more preferably 1 to 6. In this case, although there are no particular limitations on the amino acid sequence of that portion following deletion, substitution or addition, the ratio of the number of net basic amino acid residues to the number of amino acid residues that compose said portion preferably exceeds 14.5%. This is because if the ratio of the number of net basic amino acid residues to the total number of amino acid residues in said portion exceeds 14.5%, in addition to demonstrating antitumor action against cells exhibiting sensitivity to TNF (for example, L-929 cells), antitumor action is also demonstrated against cells that do not exhibit any sensitivity to TNF (for example, T-24 cells (Science, Vol. 230, pp. 943-945 (1985)) (Japanese Patent No. 2544114).

Polypeptides to which a sugar chain has been added and polypeptides to which a sugar chain has not been added are included in polypeptides (a) and (b). Although the types, locations and so on of the sugar chain added to the polypeptide vary according to the type of host cells used during polypeptide production, polypeptides obtained using any host cells are included in polypeptides to which a sugar chain has been added. In addition, pharmaceutically acceptable salts are also included in polypeptides (a) and (b), specific examples of which include nontoxic alkaline metal salts, alkaline earth metal salts and ammonium salts such as sodium, potassium, lithium, calcium, magnesium, barium and ammonium salts. In addition, nontoxic acid addition salts resulting from reaction between a polypeptide or amino acid and a suitable organic acid or inorganic acid are also included in the above-mentioned salts. Typical examples of nontoxic acid addition salts include hydrochlorides, hydrogen chlorides, hydrogen bromides, sulfates, bisulfates, acetates, oxalates, valerates, oleates, laurates, borates, benzoates, lactates, malates, p-toluene sulfonates (tosylates), citrates, maleates, fumarates, succinates, tartrates, sulfonates, glycolates, maleates, ascorbates and benzene sulfonates.

Polypeptides (a) and (b) can be produced in accordance with ordinary methods using DNA encoding each polypeptide. DNA encoding polypeptide (a) or (b) can be obtained by chemical synthesis according to the nucleotide sequence thereof. Chemical synthesis of DNA can be carried out using a commercially available DNA synthesizer such as a DNA synthesizer using the thiophosphite method (Shimadzu) or a DNA synthesizer using the phosphamidite method (Perkin-Elmer). In addition, DNA encoding polypeptide (a) or (b) can be obtained by artificially inserting a mutation into DNA encoding the 4th exon of TNF-α by site-specific mutagenesis and so on. Mutation insertion can be carried out, for example, by using a mutation insertion kit such as Mutant-K (Takara), Mutant-G (Takara) or a kit of the LA-PCR In Vitro Mutagenesis Series (Takara).

Polypeptides (a) and (b) can be produced according to the process described below by expressing DNA that encodes each polypeptide in host cells.

[Production of Recombinant Vector and Transformants]

When producing a recombinant vector, a DNA fragment is prepared of a suitable length that contains a region that encodes the target polypeptide. In addition, DNA in which nucleotides have been substituted is prepared so that the nucleotide sequence of the region that encodes the target polypeptide is the optimum codon for expression in host cells.

A transformant capable of producing the target polypeptide can be obtained by producing a recombinant vector by inserting this DNA fragment downstream from a suitable expression vector promoter followed by inserting said recombinant vector into suitable host cells. The above-mentioned DNA fragment is required to be incorporated in a vector so as to demonstrate the function thereof, and in addition to a promoter, the vector can contain a cis element such as an enhancer, splicing signal, poly A addition signal, selection marker (such as dihydrofolate reductase gene, ampicillin resistance gene or neomycin resistance gene) or ribosome binding sequence (SD sequence).

There are no particular limitations on the expression vector provided it is able to self-replicate in the host cells, and examples of expression vectors that can be used include plasmid vectors, phage vectors and virus vectors. Examples of plasmid vectors include plasmids originating in *Escherichia coli* (such as pRSET, pBR322, pBR325, pUC118, pUC119, pUC118 and pUC119), plasmids originating in *Bacillus subtilis* (such as pUB110 and pTP5), and plasmids originating in yeast (such as YEp13, YEp24 and YCp50). Examples of phage vectors include λ phages (such as Charon4A, Charon21A, EMBL3, EMBL4, λgt10, λgt11 and λZAP). Examples of virus vectors include animal viruses such as retrovirus, vaccinia virus and adenovirus, and insect viruses such as baculovirus.

Any cells such as prokaryotic cells, yeast, animal cells, insect cells or plant cells may be used for the host cells provided they are able to express the target gene. In addition, animal individuals, plant individuals or silkworm bodies and so on may also be used.

In the case of using bacteria for the host cells, *Escherichia* species such as *Escherichia coli*, *Bacillus* species such as *Bacillus subtilis*, *Pseudomonas* species such as *Pseudomonas putida* or *Rhizobium* species such as *Rhizobium meliloti* and so on can be used as host cells. More specifically, *Escherichia coli* strains such as *Escherichia coli* XL1-Blue, *Escherichia coli* XL2-Blue, *Escherichia coli* DH1, *Escherichia coli* K12, *Escherichia coli* JM109 and *Escherichia coli* HB101, or *Bacillus subtilis* strains such as *Bacillus subtilis* MI114 and *Bacillus subtilis* 207-21 can be used as host cells. There are no particular limitations on the promoter used in this case provided they are able to express in bacteria such as *Escherichia coli*, and examples of promoters that can be used include trp promoter, lac promoter, $P_L$ promoter, $P_R$ promoter and other promoters originating in *Escherichia coli* and phages. In addition, artificially altered promoters such as tac promoter, lacT7 promoter and let I promoter can also be used.

There are no particular limitations on the method for inserting a recombinant vector into bacteria provided it allows the insertion of DNA into bacteria, and examples of methods that can be used include methods using calcium ions and electroporation.

In the case of using yeast for the host cells, yeasts such as *Saccharomyces cerevisiae*, *Schizosaccharomyces pombe* and *Pichia pastoris* can be used as host cells. There are no particular limitations on the promoter in this case provided it is able to express in yeast, and examples of promoters that can be used include gal1 promoter, gal10 promoter, heat shock protein promoter, MFα1 promoter, PH05 promoter, PGK promoter, GAP promoter, ADH promoter and A0X1 promoter.

There are no particular limitations on the method for inserting a recombinant vector into yeast provided it allows the insertion of DNA into yeast, and examples of methods that can be used include electroporation, the spheroplast method and the lithium acetate method.

In the case of using animal cells for the host cells, monkey COS-7 cells, Vero cells, Chinese hamster ovary cells (CHO cells), mouse L cells, rat GH3 cells, human FL cells and so on can be used as host cells. There are no particular limitations on the promoter in this case provided it is able to express in animal cells, and examples of promoters that can be used include SRα promoter, SV40 promoter, LTR (Long Terminal Repeat) promoter, CMV promoter and human cytomegalovirus early gene promoter.

There are no particular limitations on the method for inserting a recombinant vector into animal cells provided it allows the insertion of DNA into animal cells, and examples of methods that can be used include electroporation, the calcium phosphate method and lipofection.

In the case of using insect cells for the host cells, the ovary cells of *Spodoptera frugiperda*, the ovary cells of *Trichoplusia ni* or cultured cells originating in silkworm ovary and so on can be used as host cells. Examples of ovary cells of *Spodoptera frugiperda* include Sf9 and Sf21, examples of ovary cells of *Trichoplusia ni* include High 5 and BTI-TN-5B1-4 (Invitrogen), and examples of cultured cells originating in silkworm ovary include *Bombyx mori* N4.

There are no particular limitations on the method for inserting a recombinant vector into insect cells provided it allows insertion of DNA into insect cells, and examples of methods that can be used include the calcium phosphate method, lipofection and electroporation.

[Culturing of Transformants]

A transformant that has been inserted with a recombinant vector incorporating DNA that encodes a target polypeptide is cultured in accordance with ordinary culturing methods. Culturing of transformants can be carried out in accordance with ordinary methods used for culturing host cells.

Any natural or synthetic medium may be used for the medium used to culture transformants obtained by using microorganisms such as *Escherichia coli* or yeasts as the host cells provided it contains a carbon source, nitrogen source or inorganic salt and so on that can be assimilated by the microorganisms, and enables transformants to be cultured efficiently.

Examples of carbon sources that can be used include carbohydrates such as glucose, fructose, sucrose and starch, organic acids such as acetic acid and propionic acid, alcohols such as ethanol and propanol. Examples of nitrogen sources that can be used include ammonia and ammonium salts of inorganic acids or organic acids such as ammonium chloride, ammonium sulfate, ammonium acetate and ammonium phosphate, peptone, beef extract, yeast extract, corn stiplica and casein hydrolysates. Examples of inorganic salts that can be used include potassium dihydrogen phosphate, dibasic potassium phosphate, magnesium phosphate, magnesium sulfate, sodium chloride, ferrous sulfate, manganese sulfate, copper sulfate and calcium carbonate.

Culturing of transformants is carried out under aerobic conditions in the form of shake culturing or aeration culturing. The culturing temperature is normally 28 to 37° C., the culturing time is normally 0.5 to 4 days, and the pH is maintained between 6.8 and 7.5 during the culturing period. Adjustment of pH can be carried out using inorganic acid, organic acid, alkaline solution, urea, calcium carbonate or ammonium and so on. In addition, antibiotics such as ampicillin or tetracycline may be added to the medium as necessary during culturing.

When culturing microorganisms transformed with an expression vector using an inducible promoter as the promoter, an inducer may be added to the medium as necessary. For example, when culturing microorganisms transformed with an expression vector using lac promoter, an inducer such as isopropyl-β-D thiogalactopyranoside may be added to the medium, and when culturing microorganisms transformed with an expression vector using trp promoter, indole acrylic acid may be added to the medium.

Commonly used RPMI1640 medium, Eagle's MEM medium, α-MEM medium, DMEM medium or media to which fetal calf serum and so on has been added to these media can be used as media for culturing transformants obtained by using animal cells for the host cells. Culturing of transformants is normally carried out at 37° C. for 2 to 20 days in the presence of 5% $CO_2$. In addition, antibiotics such as kanamycin, penicillin, streptomycin, neomycin, hygromycin or blasticidin and so on may be added to the medium as necessary during culturing.

Examples of media that can be used for the medium when culturing transformants obtained by using insect cells for the host cells include commonly used TNM-FH medium (Pharminogen), TC-100 medium (Gibco BRL), Sf-900 II SFM medium (Gibco BRL), ExCell400 and ExCell405 (JRH Biosciences). Culturing of transformants is normally carried out at 22 to 28° C. for 3 to 20 days. In addition, antibiotics such as gentamycin may be added to the medium as necessary during culturing.

[Polypeptide Isolation and Purification]

A target polypeptide can be obtained by collecting the target polypeptide from a culture of transformants. Here, a culture supernatant, cultured cells, cultured microorganisms and crushed cells or microorganisms are all included in a "culture".

In the case the target polypeptide is accumulated in cells of the transformants, the cells in the culture are collected by centrifugal separation of the culture, crushing the cells after washing said cells, and then extracting the target polypeptide. In the case the target polypeptide is excreted outside the cells, either the culture supernatant is used directly, or the cells or microorganisms are removed from the culture supernatant by centrifugal separation and so on.

Polypeptide (a) or (b) obtained in this manner can be purified by, for example, solvent extraction, salting out or desalting using ammonium sulfate, precipitation using an organic solvent, diethylaminoethyl (DEAE)-sepharose, ion exchange chromatography, hydrophobic chromatography, gel filtration or affinity chromatography.

Polypeptide (a) or (b) can be produced by a chemical synthesis method such as the Fmoc method (fluoronyl methoxy carbonyl method), or the tBoc method (t-butoxy carbonyl method). At this time, a commercially available peptide synthesizer can be used.

Although the malignant glioma antitumor agent of the present invention may be composed of only polypeptide (a) or polypeptide (b), it is normally formulated in accordance with ordinary methods with one more types of pharmaceutically acceptable carriers and/or additives. Although the blended amount of polypeptide (a) or (b) can be suitably adjusted when formulating, it is normally $10^4$ to $10^9$ U/mg, and preferably within the range of usage precedents. Examples of usage precedents include the interferon α preparation, Roferon A600 (Chugai Pharmaceutical, Roferon A: 600 IU, human serum albumin: 5 mg, sodium chloride: 9 mg), and the erythropoietin preparation, Epogin 90 (Chugai Pharmaceutical, genetically modified epoetin beta: 9000 IU, L-histidine hydrochloride: 0.675 mg, polysorbate 80: 0.025 mg) (Japanese Pharmaceutical Excipients Directory 2000, Japan Pharmaceutical Excipients Council).

Examples of pharmaceutically acceptable carriers include water, pharmaceutically acceptable organic solvents, collagen, polyvinyl alcohol, polyvinyl pyrrolidone, carboxyvinyl polymers, sodium alginate, water-soluble dextran, sodium carboxymethyl starch, pectin, xanthan gum, gum Arabic, casein, gelatin, agar, glycerin, propylene glycol, polyethylene glycol, vaseline, paraffin, stearyl alcohol, stearic acid, human serum albumin, mannitol, sorbitol and lactose.

Examples of additives used during formulation include vehicles, disintegration agents, correctives, fillers, thickeners, binders, moisturizers, surface activators, lubricants, stabilizers, antimicrobials, buffers, isotonic agents, chelating agents, pH adjusters and surfactants, and these additives are suitably selected according to the form of the administration units of the preparation and so on.

Examples of administration routes include oral administration and parenteral administration such as intracerebral administration, intraperitoneal administration, intraoral administration, intratracheal administration, rectal administration, subcutaneous administration, intramuscular administration and intravenous administration. In addition, examples of administration forms include tablets, powders, injections, granules, sprays, capsules, syrups, emulsions, suppositories, ointments and tapes.

Although dosage and the number of administrations are determined on an individual basis in consideration of the age, symptoms, body weight and administration effects of the patient or animal being dosed under the strict supervision of a supervising physician or veterinarian, in the case of a human adult (body weight: 60 kg), the general reference for the daily dosage in the case of venous administration is 1 million units, that in the case of arterial administration is 2 million units, and that in the case of transcutaneous administration is 1 million units, and this daily dosage can be administered all at once or divided among several administrations per day. Furthermore, in the case of animals other than humans such as cow, horses or other large animals, the general reference for the daily dosage is 1/60th the above-mentioned human daily dosage per kg of body weight, while in the case of chickens and other birds, the general reference for the daily dosage is roughly twice that amount per kg of body weight.

The above-mentioned units are determined in the following manner based on cytotoxicity to L-929 cells of each polypeptide using as an indicator the specific activity of TNF-α as standardized by WHO (Proceedings of the National Academy of Science of the United States of America, 1975, Vol. 72, pp. 3666-3670).

L-929 cells are grown in Eagle's minimum essential medium (MEM) containing 5% fetal calf serum, and disseminated into a 96-well flat bottom plate so that $8 \times 10^4$ cells are contained in 100 μL of the same medium. The cells are incubated under conditions of 37° C. for 2 hours at 5% $CO_2$ and 100% $H_2O$, and a method used for ordinary cell culturing may be used. Subsequently, actinomycin D is added to the medium to a final concentration of 1 μg/mL and the volume of the culture broth is brought to a volume of 150 μL (actinomycin D is a drug frequently used to enhance cell sensitivity, and itself is not toxic to L-929 cells). Immediately thereafter, 50 μL of specimen suitably diluted with MEM medium are added (the $ED_{50}$ value can be determined by suitably adjusting the dilution factor at this time). Moreover, the L-929 cells in a final broth volume of 200 μL are incubated for 18 hours under the above-mentioned conditions.

When measuring cell necrotic activity, all of the medium is first removed followed by the addition of 2% methyl alcohol solution containing 0.2% crystal violet to fix and stain the cells. Crystal violet stains all nucleated cells, and since cells that have separated from the bottom of the plate as a result of the occurrence of cell necrosis are not stained, cell necrotic activity can be measured directly. This degree of staining is measured by absorption at $OD_{590nm}$, and cell necrotic activity is measured by comparing with the degree of staining with respect to a control group. Activity is defined in the manner described below.

The dilution factor (N) of a specimen in which 50% of the L-929 cells are able to survive is determined. Rabbit TNS are used for the control, and the activity n (units/mL) of the rabbit TNS is determined using $2.4 \times 10^6$ units/mg/mL of TNF-α. The dilution factor (C) that yields the $ED_{50}$ of this rabbit TNS is then determined.

Specimen activity (units/mL) is calculated based on N/C× n.

The $LD_{50}$ values in mice of the polypeptide composed of the amino acid sequence described in SEQ ID NO: 1 are $9.5 \times 10^7$ units/kg (BALB/C strain), $2.7 \times 10^7$ units/kg (C3H/He strain) and $5.8 \times 10^7$ units/kg (C57BL/6 strain), while the $LD_{50}$ values in mice of the polypeptide composed of the amino acid sequence described in SEQ ID NO: 2 are $2.9 \times 10^7$ units/kg (BALB/C strain), $2.7 \times 10^7$ units/kg (C3H/He strain) and $2.7 \times 10^7$ units/kg (C57BL/6 strain). The values for both of these polypeptides are extremely small in comparison with the values of TNF-α of $1.0 \times 10^7$ units/kg (BALB/C strain), $7.8 \times 10^6$ units/kg (C3H/He strain) and $5 \times 10^7$ units/kg (C57BL/6 strain). In this manner, the extremely low level of toxicity of polypeptide (a) or (b) to normal cells as compared with TNF-α also enhances the usefulness in the clinical setting of the pharmaceutical composition of the present invention.

Malignant glioma in humans or animals can be prevented or treated by administering the pharmaceutical composition of the present invention to humans or animals. Malignant gliomas include anaplastic astrocytoma, glioblastoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor and a typical teratoid/rhabdoid tumor. Examples of animals include mammals such as cows, sheep, goats, horses, pigs, rabbits, dogs, cats, rats and mice, and birds such as chickens.

EXAMPLES

The following provides a detailed explanation of the present invention through production examples and test examples. Furthermore, the polypeptide composed of the amino acid sequence described in SEQ ID NO: 1 is referred to as "TNF-SAM1", while the polypeptide composed of the amino acid sequence described in SEQ ID NO: 2 is referred to as "TNF-SAM2".

Production Example 1—Injection $1 \times 10^6$ units (approx. 250 μg) of TNF-SAM1, TNF-SAM2 or a mixture thereof was dissolved in 1 mL of physiological saline to prepare an injection solution.

Production Example 2—Slow-Release Preparation $1 \times 10^6$ units (approx. 250 μg) of TNF-SAM1, TNF-SAM2 or a mixture thereof was classified and injected into liposomes to prepare a slow-release preparation.

Test Example 1

The malignant glioma antitumor action of TNF-SAM2 was investigated according to the life-prolonging effects in gliomatous rats in which glioma cells in the form of C6 glioma cells were transplanted into rat cerebral ventricle.

After anesthetizing the rats (5-week-old, male Wistar rats, body weights: 150 to 250 g) and performing craniectomy using a cerebral stereotaxic insertion device, a solution in which $1.6 \times 10^4$ C6 glioblastoma cells (brain tumor cells) were suspended in 5 μL of physiological saline was injected into the brain to a depth of 4 mm. The rats were used as brain tumor model rats on the third day after transplantation of brain tumor cells. Five brain tumor transplant rats each were used in each dose group (Group A: normal rat serum, Group B: TNF-α, Group C: TNF-SAM2). In each dose group, specimens were prepared so as to contain 3% normal rat serum, and the animals were dosed once from the carotid artery.

The results are shown in Table 1.

TABLE 1

| Dose Group | Specimen | Dosage (units/administration/animal) | 50% survival duration (days) |
|---|---|---|---|
| A | Normal rat serum | | 19.0 |
| B | TNF-α + normal rat serum | $2 \times 10^6$ | 17.4 |
| | | $7 \times 10^6$ | 0 |
| | | $20 \times 10^6$ | 0 |
| C | TNF-SAM2 + normal rat serum | $2 \times 10^6$ | 17.8 |
| | | $7 \times 10^6$ | 20.6 |
| | | $20 \times 10^6$ | 16.4 |

As shown in Table 1, in addition to TNF-α not having any antitumor effects whatsoever, it also resulted in death earlier than in the drug non-dose group (Group A) at dosages of $7 \times 10^6$ and $20 \times 10^6$ units. In contrast, TNF-SAM2 demonstrated significant life-prolonging effects compared with the drug non-dose group (Group A) and the TNF-α dose group (Group B) at a dosage of 7×10⁶ units.

Furthermore, since TNF-SAM2 has been reported to synergistically demonstrate antitumor effects during concomitant use with alkylating agents (Cancer Biotherapy, Vol. 9, pp. 359-367 (1994)), concomitant therapy of temozolomide and TNF-SAM2 is predicted to be effective against malignant glioma.

Example 2

(1) Case 1

Although surgery was performed on a 47-year-old woman found to have anaplastic astrocytoma (grade III) in 2001, the tumor was only partially removed. This patient was administered 100 mg of Ranimustin ((methyl-6)-3-(2-chloroethyl)-3-(nitrosoureido)-6-deoxy-alpha-D-glucopyranoside: MCNU) on day 1 followed by radiotherapy, and then administered 1 million units of TNF-SAM2 five times a week starting on day 3. When this treatment was performed 15 times, the brain tumor was shown by MRI to have reduced in size by 50% or more.

(2) Case 2

Although a 50-year-old woman found to have glioblastoma (grade IV) in 1997 underwent radical sub-total resection, the tumor remained. The same treatment as that described above was performed for 5 weeks. There was no growth of the residual tumor during that time.

The invention claimed is:

1. A pharmaceutical composition for treating malignant glioma comprising a polypeptide comprising the amino acid sequence represented by SEQ ID NO:1 or SEQ ID NO:2.

2. The pharmaceutical composition according to claim 1, which is a pharmaceutical composition for animals.

3. A method for treating malignant glioma comprising: administering to humans or animals the composition of claim 1.

4. The method of claim 3, wherein the malignant glioma is anaplastic astrocytoma, glioblastoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, or atypical teratoid/rhabdoid tumor.

5. The method of claim 3, further comprising administration of an alkylating agent.

6. The composition of claim 1 which is a liposomal composition.

* * * * *

SEQUENCE LISTING

```
<160> NUMBER OF SEQ ID NOS: 3

<210> SEQ ID NO 1
<211> LENGTH: 158
<212> TYPE: PRT
<213> ORGANISM: Artificial Sequence
<220> FEATURE:
<223> OTHER INFORMATION: human TNF mutain

<400> SEQUENCE: 1

Met Val Arg Ser Ser Thr Arg Thr Pro Ser Arg Lys Pro Val Ala His
 1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155

<210> SEQ ID NO 2
<211> LENGTH: 158
<212> TYPE: PRT
<213> ORGANISM: Artificial Sequence
<220> FEATURE:
<223> OTHER INFORMATION: human TNF mutain

<400> SEQUENCE: 2

Met Val Arg Ser Cys Thr Arg Thr Pro Ser Arg Lys Pro Val Ala His
 1               5                   10                  15

Val Val Ala Asn Pro Gln Ala Glu Gly Gln Leu Gln Trp Leu Asn Arg
            20                  25                  30
```

-continued

```
Arg Ala Asn Ala Leu Leu Ala Asn Gly Val Glu Leu Arg Asp Asn Gln
             35                  40                  45

Leu Val Val Pro Ser Glu Gly Leu Tyr Leu Ile Tyr Ser Gln Val Leu
     50                  55                  60

Phe Lys Gly Gln Gly Cys Pro Ser Thr His Val Leu Leu Thr His Thr
 65                  70                  75                  80

Ile Ser Arg Ile Ala Val Ser Tyr Gln Thr Lys Val Asn Leu Leu Ser
             85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
            115                 120                 125

Lys Gly Asp Arg Leu Ser Ala Glu Ile Asn Arg Pro Asp Tyr Leu Asp
        130                 135                 140

Phe Ala Glu Ser Gly Gln Val Tyr Phe Gly Ile Ile Ala Leu
145                 150                 155

<210> SEQ ID NO 3
<211> LENGTH: 422
<212> TYPE: DNA
<213> ORGANISM: Homo sapiens

<400> SEQUENCE: 3
caaaccctca agctgagggg cagctccagt ggctgaaccg ccgggccaat gccctcctgg      60
ccaatggcgt ggagctgaga gataaccagc tggtggtgcc atcagagggc ctgtacctca     120
tctactccca ggtcctcttc aagggccaag gctgcccctc acccatgtg ctcctcaccc      180 acaccatcag ccgcatcgcc gtctcctacc agaccaaggt caacctcctc tctgccatca     240 agagccctg ccagagggag accccagagg gggctgaggc caagccctgg tatgagccca     300
tctatctggg aggggtcttc cagctggaga agggtgaccg actcagcgct gagatcaatc     360
ggcccgacta tctcgacttt gccgagtctg ggcaggtcta ctttgggatc attgccctgt     420
ga                                                                    422
```